US010272236B2

(12) United States Patent
Davey

(10) Patent No.: US 10,272,236 B2
(45) Date of Patent: Apr. 30, 2019

(54) DEFORMABLE MEDICAL IMPLANT

(71) Applicant: Christopher Davey, Galway (IE)

(72) Inventor: Christopher Davey, Galway (IE)

(73) Assignee: Marvao Medical Devices Ltd, Galway (IE)

( * ) Notice: Subject to any disclaimer, the term of this patent is extended or adjusted under 35 U.S.C. 154(b) by 275 days.

(21) Appl. No.: 15/088,409

(22) Filed: Apr. 1, 2016

(65) Prior Publication Data

US 2016/0213909 A1 Jul. 28, 2016

Related U.S. Application Data

(60) Continuation-in-part of application No. 14/090,246, filed on Nov. 26, 2013, now Pat. No. 9,302,088, (Continued)

(51) Int. Cl.
*A61M 39/02* (2006.01)
*A61B 17/50* (2006.01)

(52) U.S. Cl.
CPC ......... *A61M 39/0247* (2013.01); *A61B 17/50* (2013.01); *A61M 39/0208* (2013.01);
(Continued)

(58) Field of Classification Search
CPC .......... A61B 17/50; A61M 2039/0223; A61M 2039/0232; A61M 2039/0261; A61M 2039/0273; A61M 2039/0279; A61M 2039/0291; A61M 39/0208; A61M 39/0247

See application file for complete search history.

(56) References Cited

U.S. PATENT DOCUMENTS 3,663,965 A   5/1972   Lee et al.
3,752,162 A   8/1973   Newash
(Continued)

FOREIGN PATENT DOCUMENTS

WO   2007085907   8/2007

OTHER PUBLICATIONS

Raad, et al., Arch Internal Medicine, "Intravascular Catheter-Related Infections: New Horizons and Recent Advances", vol. 162, pp. 871-878, Apr. 2002.
(Continued)

*Primary Examiner* — Imani N Hayman
(74) *Attorney, Agent, or Firm* — David Silverstein; Onello & Mello, LLP

(57) ABSTRACT

The present invention comprises a deformable, implantable subcutaneous port for anchoring a transcutaneous treatment component. A port body portion having a normal area port footprint is adapted by means of a port orifice for receiving and anchoring the transcutaneous treatment component beneath the point of entry into the physiology of a patient and for routing the transcutaneous treatment component. The port body portion is produced from a deformable material and has structure and/or composition that provides deformability characteristics of the port such that collapsing, folding, stretching, elongating and/or twisting the port body portion into a modified port shape having a reduced-size port profile enables removal of the port body portion from the physiology of a patient through a relatively small transcutaneous opening.

13 Claims, 14 Drawing Sheets

Related U.S. Application Data which is a division of application No. 12/412,464, filed on Mar. 27, 2009, now Pat. No. 8,617,116.

(52) U.S. Cl.
CPC .............. *A61M 2039/0223* (2013.01); *A61M 2039/0232* (2013.01); *A61M 2039/0261* (2013.01); *A61M 2039/0273* (2013.01); *A61M 2039/0279* (2013.01); *A61M 2039/0291* (2013.01)

(56) References Cited

U.S. PATENT DOCUMENTS

| | | |
|---|---|---|
| 4,004,298 A | 1/1977 | Freed |
| 4,134,402 A | 1/1979 | Mahurkar |
| 4,266,999 A | 5/1981 | Baier |
| 4,321,914 A | 3/1982 | Begovac et al. |
| 4,327,722 A | 5/1982 | Groshong et al. |
| 4,327,732 A | 5/1982 | Groshong et al. |
| 4,405,305 A | 9/1983 | Stephen et al. |
| 4,488,877 A | 12/1984 | Klein et al. |
| 4,578,063 A | 3/1986 | Inman et al. |
| 4,583,968 A | 4/1986 | Mahurkar |
| 4,634,422 A | 1/1987 | Kantrowitz et al. |
| 4,654,033 A | 3/1987 | Lapeyre et al. |
| 4,668,222 A | 5/1987 | Poirier |
| 4,673,394 A | 6/1987 | Fenton, Jr. et al. |
| 4,676,782 A | 6/1987 | Yamamoto et al. |
| 4,808,155 A | 2/1989 | Mahurkar |
| 4,886,502 A | 12/1989 | Poirier et al. |
| 4,897,081 A | 1/1990 | Poirier et al. |
| 4,898,669 A | 2/1990 | Tesio |
| 4,935,004 A | 6/1990 | Cruz |
| 4,959,054 A | 9/1990 | Heimke et al. |
| 5,084,024 A | 1/1992 | Skinner |
| 5,098,397 A | 3/1992 | Svensson et al. |
| 5,100,392 A | 3/1992 | Orth et al. |
| 5,156,597 A | 10/1992 | Verreet et al. |
| 5,171,216 A | 12/1992 | Dasse et al. |
| 5,242,415 A | 9/1993 | Kantrowitz et al. |
| 5,562,618 A | 10/1996 | Cai et al. |
| 5,624,392 A | 4/1997 | Saab |
| 5,662,616 A | 9/1997 | Bousquet |
| 5,685,878 A | 11/1997 | Falwell et al. |
| 5,700,477 A | 12/1997 | Rosenthal et al. |
| 5,718,678 A | 2/1998 | Fleming, III |
| 5,718,692 A | 2/1998 | Schon et al. |
| 5,743,873 A | 4/1998 | Cai et al. |
| 5,766,249 A | 6/1998 | Griffith |
| 5,776,111 A | 7/1998 | Tesio |
| 5,823,994 A | 10/1998 | Sharkey et al. |
| 5,830,184 A | 11/1998 | Basta |
| 5,848,987 A | 12/1998 | Baudino et al. |
| 5,882,341 A | 3/1999 | Bousquet |
| 5,902,268 A | 5/1999 | Saab |
| 5,947,953 A | 9/1999 | Ash et al. |
| 5,989,213 A | 11/1999 | Maginot |
| 6,033,382 A | 3/2000 | Basta |
| 6,050,979 A | 4/2000 | Haemmerle et al. |
| 6,099,508 A | 8/2000 | Bousquet |
| 6,117,163 A | 9/2000 | Bierman |
| 6,190,349 B1 | 2/2001 | Ash et al. |
| 6,238,369 B1 | 5/2001 | Burbank et al. |
| 6,264,673 B1 | 7/2001 | Egnelov et al. |
| 6,355,020 B1 | 3/2002 | Bousquet |
| 6,471,689 B1 | 10/2002 | Joseph et al. |
| 6,520,949 B2 | 2/2003 | St. Germain |
| 6,595,966 B2 | 7/2003 | Davey et al. |
| 6,605,063 B2 | 8/2003 | Bousquet |
| 6,638,242 B2 | 10/2003 | Wilson et al. |
| 6,682,519 B1 | 1/2004 | Schon |
| 6,695,832 B2 | 2/2004 | Schon et al. |
| 6,719,724 B1 | 4/2004 | Walker et al. |
| 6,719,749 B1 | 4/2004 | Schweikert et al. |
| 6,872,198 B1 | 3/2005 | Wilson et al. |
| 6,969,381 B2 | 11/2005 | Voorhees |
| 7,014,623 B2 | 3/2006 | Prestidge et al. |
| 7,018,374 B2 | 3/2006 | Schon et al. |
| 7,811,257 B2 | 10/2010 | Saab |
| 2003/0229323 A1 | 12/2003 | Haarala et al. |
| 2004/0181240 A1 | 9/2004 | Tseng et al. |
| 2004/0204687 A1 | 10/2004 | Mogensen et al. |
| 2004/0236314 A1 | 11/2004 | Saab |
| 2005/0107753 A1 | 5/2005 | Rezai et al. |
| 2005/0208095 A1 | 9/2005 | Hunter et al. |
| 2006/0135946 A1 | 6/2006 | Moehle et al. |
| 2006/0241737 A1 | 10/2006 | Tockman et al. |
| 2007/0043323 A1 | 2/2007 | Davey |
| 2007/0060891 A1 | 3/2007 | Skiera |
| 2007/0066966 A1 | 3/2007 | Davey |
| 2007/0219510 A1 | 9/2007 | Zinn et al. |
| 2007/0225642 A1 | 9/2007 | Houser et al. |
| 2008/0140003 A1 | 6/2008 | Bei et al. |
| 2009/0131919 A1 | 5/2009 | Davey |

OTHER PUBLICATIONS

"Deformable Medical Implant" Specification, Drawings and Prosecution History, of U.S. Appl. No. 12/412,464, filed Mar. 27, 2009, by Christopher Davey.

Fanous et al., "Dacron Implants for Rhinoplasty" Arch Facial Plast. Surg. vol. 4, Jul.-Sep. 2002, pp. 149-156.

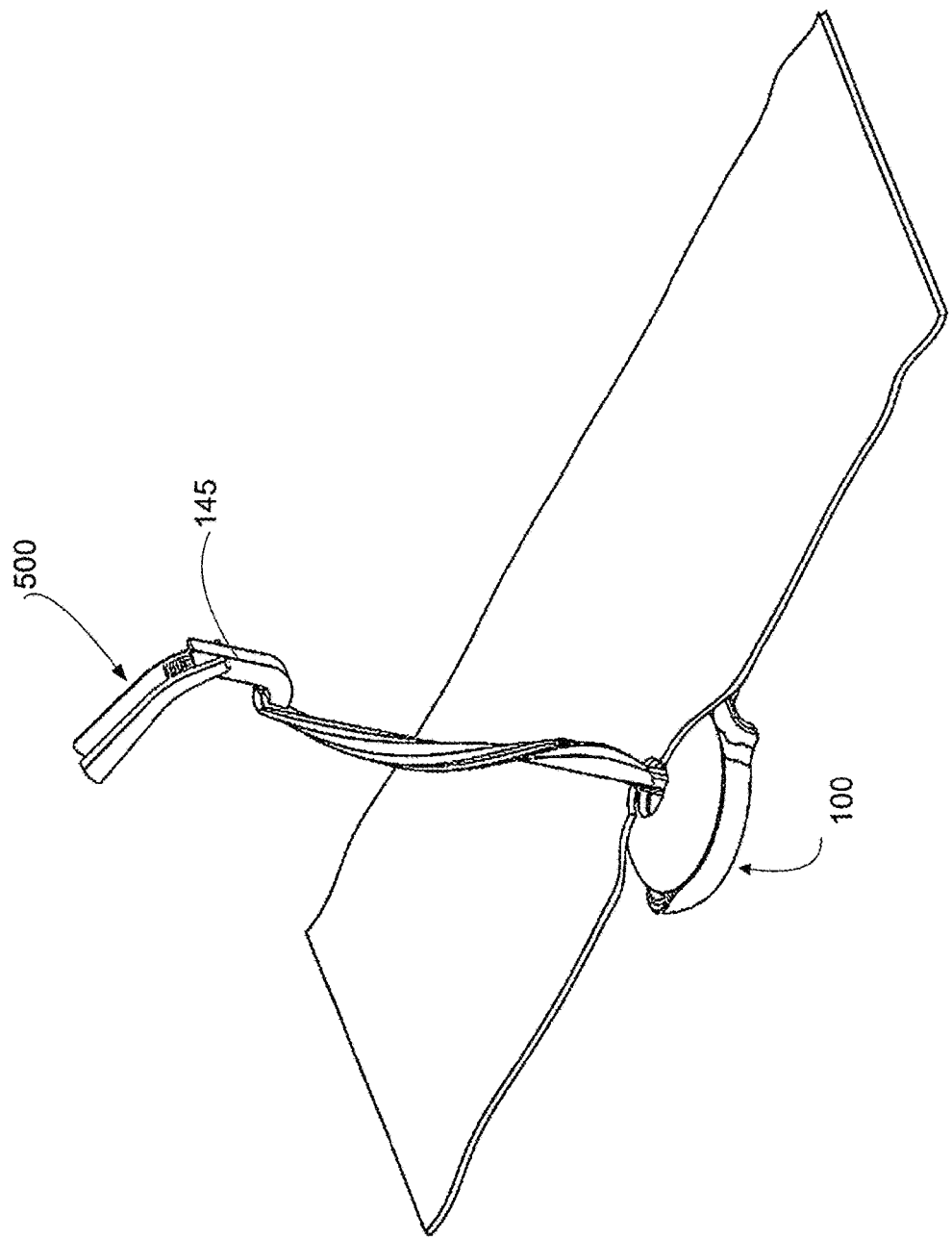

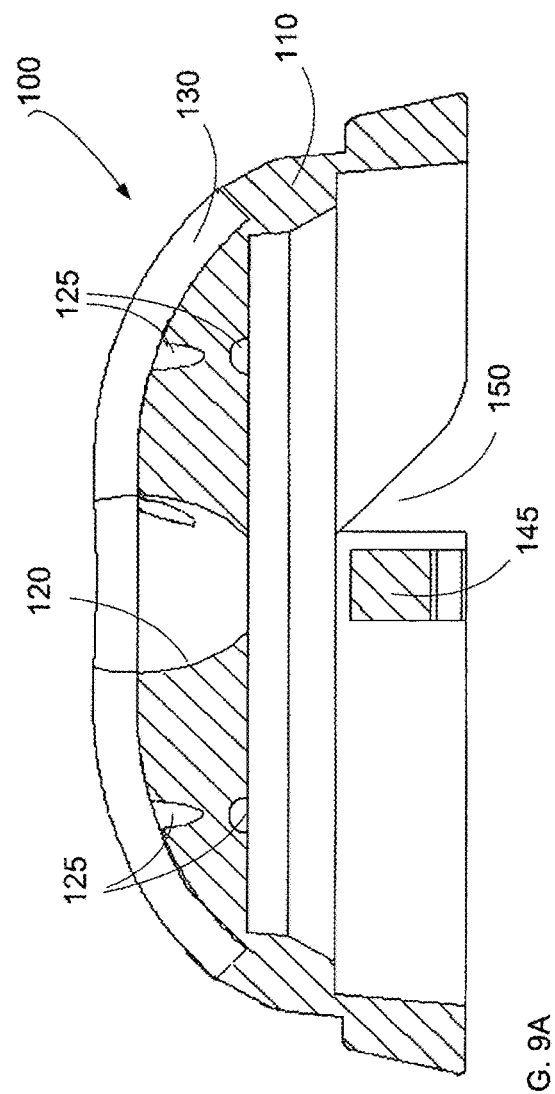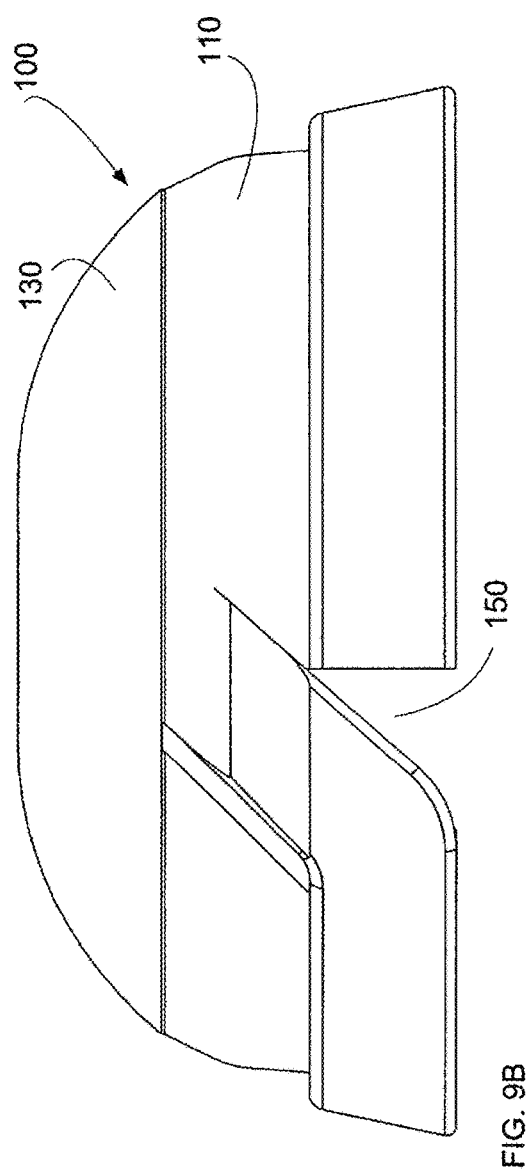

DEFORMABLE MEDICAL IMPLANT

CROSS-REFERENCE TO RELATED APPLICATIONS

This application claims benefit of the filing dates of U.S. patent application Ser. No. 14/090,246, filed Nov. 26, 2013, now pending, which is a Division of U.S. patent application Ser. No. 12/412,464, filed Mar. 27, 2009, now U.S. Pat. No. 8,617,116. The complete contents of the preceding earlier applications are incorporated herein by reference.

BACKGROUND OF THE INVENTION

1. Field of the Invention

The present invention relates generally to the field of medical devices. In particular, the present invention relates to long term, implantable devices that permits access to inner physiology and that enable non-traumatic removal following treatment.

2. Summary of the Related Art

Medically treating a patient often requires long term placement of a medical device across one or more organ systems to establish access to a specifically targeted interior body site for diagnostic or therapeutic purposes. One common example is the establishment of percutaneous vascular access for purposes of administering liquid therapeutic agents, removing bodily fluids for testing or monitoring, treating bodily fluids before being returned to the body, and/or disposing of bodily fluids.

Particularly in the case of administering fluids to the body or removing fluids from the body continuously or periodically over an extended time period, those skilled in the medical arts typically use what are known as "permanent" catheterization techniques. These techniques employ implanted devices such as tunneled central venous catheters (CVCs) that remain implanted for durations ranging from a few weeks to years. Examples of such implanted and related medical devices exist in the following references, which are incorporated herein by reference: U.S. Pat. No. 4,266,999 (Baier); U.S. Pat. No. 4,405,305 (Stephen et al.); U.S. Pat. No. 4,488,877 (Klein et al.); U.S. Pat. No. 4,668,222 (Poirier); U.S. Pat. No. 4,897,081 (Poirier et al.); U.S. Pat. No. 4,935,004 (Cruz); U.S. Pat. No. 5,098,397 (Svensson et al.); U.S. Pat. No. 5,100,392 (Orth et al.); U.S. Pat. No. 5,242,415 (Kantrowitz et al.); U.S. Pat. No. 5,662,616 (Bousquet); U.S. Pat. No. 5,823,994 (Sharkey et al.); U.S. Pat. No. 5,830,184 (Basta); U.S. Pat. No. 5,848,987 (Baudino et al.); U.S. Pat. No. 5,882,341 (Bousquet); U.S. Pat. No. 5,989,213 (Maginot); and U.S. Pat. No. 6,033,382 (Basta). Examples of therapeutic regimens requiring such long-term continuous or periodic access to a specific internal body location include parenteral feeding, chemotherapy, antibiotic administration, dialysis, and chronic anesthesiology. Central catheterization for these types of procedures are discussed in "Vascular Access for Oncology Patients" (Gallieni et al, CA Cancer J Clin 2008 doi: 10.3322/CA.208.0015).

Generally, the type of procedure that a patient requires dictates whether a physician will utilize an acute, short term catheterization technique, or a chronic, long term catheterization technique. For example, establishing a state of general anesthesiology in preparation for a surgical procedure typically involves placing a CVC in a patient's blood vessel for a relatively short period of time, such as a few minutes to a few hours, and then removing the catheter once the surgery is finished and the patient is revived. When performing such an anesthesiology procedure, a physician commonly uses a short term catheterization technique to place a drug delivery catheter in a blood vessel of the patient.

In direct contrast to this example of short term CVC placement, a physician performing a hemodialysis procedure in a patient suffering from chronic kidney failure may place a CVC in one of the patient's blood vessels for a relatively long period of time. Such a patient typically requires dialysis sessions three times per week for an indefinitely extended period of time. Healthy kidney function ensures removal of fluid, chemicals, and wastes typically filtered from a person's blood. Hemodialysis removes these elements by sending a patient's blood to an external artificial kidney machine via the permanent vascular access, often established by placement of a long term catheter within the patient. A patient who is involved in such a hemodialysis regimen may need a catheter placed in a blood vessel for weeks, months, or years in order to provide a ready means for vascular access into that patient's bloodstream to enable these frequent life saving dialysis treatments.

Long term catheterization techniques typically entail inserting a catheter into a patient using a "tunneled catheter technique." This procedure involves inserting a long term catheter into the patient through an incision in the skin and then routing the catheter for several centimeters under the skin before entering deeper regions of the body. Despite routine use, conventional tunneled catheter designs seriously compromise the ability of a patient's skin to protect the patient's body from infection. As discussed in "Intravascular Catheter-Related Infections: New Horizons and Recent Advances" (Raad et al., Arch Internal Medicine/Vol 162, Apr. 22, 2002, Pages 871-878.), catheter-related infections are frequent events and present a potentially fatal health problem. High morbidity rate and high procedural cost are characteristics of typical long term tunneled catheter usage. The primary reason that the use of conventional catheters leads to a high rate of infection is that microorganisms enter the body through the skin incision. A conventional tunneled catheter device may include a cylindrical tissue ingrowth cuff that acts as a barrier for micro-organisms entering the body and that anchors the catheter in the subcutaneous tunnel. Such a conventional device, however, still fails to prevent undesirably high infection rates. This is because standard cuff designs are designed for positioning within a subcutaneous tunnel rather than at the skin entry site, which is the most effective location at which to position a tissue ingrowth cuff for preventing infection.

Another conventional tunneled catheter design is entirely subcutaneous. This embodiment provides an advantage over traditional transcutaneous tunneled catheter designs by eliminating the need for a continuously maintained breach in skin and thereby reducing risk of infection. These subcutaneous catheters are connected to a port disposed beneath the skin. The port is capable of accepting a needle injection of fluid and then providing fluid to the subcutaneous catheter. The port has a compressed rubber septum on its upper surface immediately below the skin which is adapted for receiving a needle therethrough and resealing under residual compressive forces once the needle is removed. These fully subcutaneous devices present drawbacks relative to conventional transcutaneous catheter systems. Particularly, large bore needles would irreparably damage the septum, and so usage is limited to procedures that require low flow rates. An example of such an implanted, subcutaneous port and catheter device is provided in U.S. Pat. No. 5,562,618 (Cai, et al).

Some transcutaneous tunneled catheter devices include adjustable epidermal tissue ingrowth cuff assemblies that enable skin to heal into the devices at their entry sites into the dermis Such devices provide reduced risk of infection, and because they require no needle punctures for gaining access to the catheter, these assemblies enable the higher flow rates associated with conventional transcutaneous tunneled catheter designs. For example, the apparatus and methods disclosed in U.S. Patent Application No. 2004/0236314 to Mark A. Saab (Saab), incorporated herein by reference, allow a physician to place a modular dermal tissue ingrowth cuff assembly precisely within a skin incision site and subsequently adjust the location of the distal (internal) tip of a catheter assembly associated with the tissue ingrowth cuff assembly. This device comprises a base (or port) having tissue ingrowth material thereon for securely anchoring the port at the incision site. A physician using such a device, therefore, has the ability to position the catheter tip precisely at the desired body site without disturbing, moving, or stressing the fixed tissue ingrowth cuff. Positioning the modular tissue ingrowth cuff at the skin incision site enables the skin to heal into the device and regain its ability to protect the patient from infection.

The use of a port with a transcutaneous catheter and skin tissue ingrowth cuff assembly has resulted in numerous improvements related to patient care and well being, but they do not anticipate or address the issue of simple and efficient removal of the port once the therapy has been completed and the device is no longer needed. U.S. Publication Number 20070043323 to Christopher Davey and U.S. patent application Ser. No. 11/986,451 also to Christopher Davey address systems and methods for facilitating removal of subcutaneous tissue ingrowth devices. (Both of these references are incorporated herein by reference). The teachings in these references address the problem of tissue becoming too firmly ingrown into tissue ingrowth scaffolds, thereby requiring blunt dissection of the tissue from the device. The inventions of the Davey references comprise tissue ingrowth scaffolds that are at least partially bioabsorbable material and/or detachable from the device so that the scaffolds remain behind when the port is removed. These easily removed devices nonetheless require that a physician create a large incision through the skin to facilitate removal of the subcutaneous implanted device, regardless of the scaffold design or material. The need to make a large incision to enable removal of the subcutaneous implant significantly prolongs the procedure, greatly increases trauma to the patient, and exposes the patient to another risk of infection as a result of the added extensive breach to the skin.

A need therefore exists for a subcutaneous port that anchors a transcutaneous conduit during a treatment period and then enables removal through a minimally sized incision in the skin that causes little or no additional trauma to the patient.

SUMMARY OF THE INVENTION

The present invention comprises a medical device consisting of a deformable medical port that is capable of implantation at an implantation site within a patient for long-term treatments, such as catheterization procedures, and methods of implanting, using and removing the device. The deformable implanted medical port of the present invention comprises a port body portion with a port orifice or passageway capable of receiving, routing, and anchoring a treatment component, such as for example a catheter shaft, fluid conduit, power cable, or fiber optic cable, that extends through the skin, through the port orifice and into the internal physiology of the patient. The port is shaped to maximize comfort, ease of installation, and stability after implantation, and thus a relatively flat or domed, and generally oval-shaped geometry is most preferable for placement and use.

In an embodiment of the deformable, implantable subcutaneous port for anchoring a transcutaneous treatment component according to this invention, the deformable, implantable subcutaneous port comprises a port body portion, an orifice that extends through the port body portion, and structural and/or compositional features that facilitate removal of the port body portion intact or piecemeal, in a single piece or in multiple pieces, from the implantation site when the port is no longer needed. The port body portion is adapted for receiving the transcutaneous treatment component beneath a point of entry into the physiology of a patient and for routing the transcutaneous treatment component. The port body portion is produced from a deformable material that comprises structure and/or composition that provides adequate stability for the port when it is in use, as well as sufficient deformability characteristics to facilitate intact or piecemeal removal, with or without tearing the port, after use of the port is completed.

In an embodiment, the deformability characteristics of the port are optimized by appropriate material selection, port size and shape, and/or other design features to produce a port with a suitable balance between rigidity (for adequate structural support) and springiness (for adequate softness, pliability and cushioning of surrounding tissue when the port is implanted and in use). Consistent with the dictionary definition, the term "springiness" as used herein refers to a port according to this invention that has a suitable degree of elasticity and resiliency.

In particular, it is recognized in the art that the dermal layer between the upper (skin-facing) surface of an implanted port and the external skin surface is typically relatively thin, sensitive and may be subject to chafing and erosion by long-term contact with an implanted port. A softer, more pliable and springy port that puts less pressure on the adjacent tissue is therefore preferred, consistent with having sufficient rigidity to maintain the necessary structural and dimensional stability of the port in use. One of ordinary skill in this art would be able to select and customize the port material and design parameters, in accordance with this invention, needed to realize an appropriate balance of port rigidity and springiness characteristics for a particular application.

The port body portion has a normal area port footprint when the port is in use. An orifice wall defines a port orifice through which the transcutaneous treatment component enters the port body portion.

In an aspect of the invention, the deformable material that comprises the port body portion has sufficient flexibility and elasticity properties such that the port can be collapsed, compressed, folded, stretched, elongated and/or twisted in situ using a suitable instrument into a modified port shape having a reduced-size port profile while the port is implanted at an implantation site.

In another aspect, the port body portion comprises at least some sections that have thinner, more flexible walls comprised of a deformable material to provide sufficient flexibility and elasticity properties such that the port can be collapsed, compressed, folded, stretched, elongated and/or twisted into a modified port shape. For example, the outer perimeter of the port body portion may be thicker to provide greater rigidity while inward wall sections are thinner or comprise structural rib members. This structure preserves operational stability of the device while maintaining port deformability characteristics to facilitate removal.

In an embodiment of this invention aspect, the port body portion is defined by a frame or cage-like structure comprised of interconnected structural ribs or support members comprising a deformable material that, because of the material composition, or because of the thickness of the structural ribs, or a combination of both, has sufficient structural rigidity to support and dimensionally stabilize the port while it is in use at an implantation site.

The structural ribs of the port frame or cage-like structure may define, for example, the perimeter of the port body portion and the contour of the upper surface of the port body portion. In some embodiments, the port frame structure comprises open spaces between the structural ribs and other frame members. In other embodiments, the open spaces between the structural members of the frame structure comprise webbing, mesh or sheets of a deformable material that, because of material composition, or because of the thinness of the webbing material, or a combination of both, is more pliable and readily deformable than the structural ribs and other frame members.

In some embodiments, the deformable materials comprising the structural members of the port frame and the webbing spanning the open spaces between those structural members comprise the same material, but the frame members are thicker and thus have greater structural stability than the webbing material. In some embodiments, the port frame or cage-like structure is covered by, or the open spaces between structural members of the frame comprise, a thin layer of a material that promotes tissue ingrowth.

In some embodiments, the deformable port body portion can be collapsed, compressed, folded, stretched, elongated and/or twisted into a modified port shape having a reduced-size port profile along an axis generally in alignment with a skin incision or transcutaneous opening. The port having the modified port shape and reduced-size port profile can then be removed substantially or entirely intact from the implantation site through a relatively small skin incision or opening. For example, the port can be removed through an opening defining an area of about 30% or less of the normal area port footprint of the port body portion, or through an opening with a maximum dimension that is about 50% or less than the largest dimension of the port when it is in use.

In another aspect, the port body portion comprises thinner wall sections along one or more regions or along frangible lines formed within the port body portion that enable removal of the port body portion from the physiology of a patient through a relatively small transcutaneous opening, such as an opening defining an area of less than about thirty percent of the normal area port footprint of the port body portion.

In another embodiment, the port of the present invention further comprises at least one frangible line extending along a continuous path between an outer perimeter of the port body portion and the orifice wall, and/or at least one gripping element disposed on the port body portion at a point adjacent to the at least one frangible line. Gripping the port body portion and/or the at least one gripping element from a point external to the body of a patient and applying port distortion force to the port body portion results in distorting the shape of the port body portion and, in some embodiments, fracturing and tearing the at least one frangible line along the continuous path between the outer perimeter of the port body portion and the annular orifice wall.

In another aspect, the port body portion comprises a material having deformability properties that change over time or under certain physical, chemical or other environmental conditions. In an embodiment, the port body portion comprises a material that chemically degrades and becomes increasingly flexible, elastic and/or pliable over time when implanted in a body as a result of exposure to bodily fluids and temperatures—i.e., a bioabsorbable or biodegradable material.

In another embodiment, the port body portion comprises a material that becomes increasingly flexible, elastic and/or pliable under slightly elevated temperature conditions. An implanted port fabricated from such a material could be gently heated to increase the port's deformability properties by, for example, circulating a heated fluid through a catheter shaft adjacent to or passing through the port.

The present invention further comprises methods for removing a deformable subcutaneous port for anchoring a transcutaneous treatment component. In one embodiment the method comprises first removing the treatment component from the deformable port, wherein the deformable port comprises a port body portion having structural and/or compositional features that facilitate removal of the port body portion from the implantation site. The port body portion is adapted for receiving the transcutaneous treatment component beneath the point of entry into the physiology of a patient and for routing the transcutaneous treatment component. The port body portion is produced from a deformable material that comprises structure and/or composition that provides adequate stability for the port when it is in use, as well as sufficient deformability characteristics to facilitate intact or piecemeal removal after use of the port is completed. The port body portion has a normal area port footprint. An orifice wall defines a port orifice through which the transcutaneous treatment component enters the port body portion.

Following the transcutaneous treatment component removal step, the method comprises inserting a port retrieval implement through the transcutaneous opening, grasping the port body portion with the retrieval implement, applying a port distortion force to the port body portion to collapse, compress, fold, stretch, elongate, twist and/or fracture the port body portion into a modified port shape having a reduced-size port profile, and pulling the port body portion having the modified port shape and the reduced-size port profile through the transcutaneous opening.

In an embodiment the invention comprises a deformable, implantable subcutaneous port for anchoring a transcutaneous treatment component comprising: a port body portion for receiving the transcutaneous treatment component beneath a point of entry into the physiology of a patient and for routing the transcutaneous treatment component, the port body portion comprising a deformable material and/or having a deformable structure with a port perimeter that defines a normal area port footprint and a port orifice through which the transcutaneous treatment component enters the port body portion; wherein the port body portion has a composition and/or structure that enables the implanted port to be collapsed, compressed, folded, stretched, elongated and/or twisted into a modified port shape having a reduced-size port profile whereby the port can be removed intact or piecemeal from the physiology of the patient through an opening that is substantially smaller than the normal area port footprint.

In an embodiment the deformable, implantable port comprises a frame or cage-like structure comprising interconnected structural members that define the port perimeter, the port orifice, and a port contour that extends between the port perimeter and the port orifice.

In an embodiment the deformable, implantable port has a port body portion that can be collapsed, compressed, folded, stretched, elongated and/or twisted into a reduced-size port profile whereby the port can be removed intact from an implantation site through a skin opening that is no larger than the size of an opening needed to accommodate the transcutaneous treatment component.

In an embodiment the deformable, implantable port comprises a frame having an appropriate balance of port rigidity and springiness to gently support and cushion the tissue adjacent the implanted port.

In an embodiment the deformable, implantable port can be collapsed, compressed, folded, stretched, elongated and/or twisted into a reduced-size port profile whereby the port can be removed intact from an implantation site through an opening that is about 50% or less than the longest dimension of the port in use, or that has an area that is about 30% or less than the normal area port footprint, or both.

In an embodiment the deformable, implantable port comprises open spaces between the structural members.

In an embodiment the deformable, implantable port comprises spaces between the structural members that define the port contour and the spaces comprise mesh, webbing or sheets of a deformable material that, because of its composition, its thickness, or both, is more pliable and deformable than the structural members.

In an embodiment the deformable, implantable port comprises mesh, webbing or sheets that span the spaces between the structural member and comprise a different deformable material than the deformable material of the structural members.

In an embodiment the deformable, implantable port comprises mesh, webbing or sheets that span the spaces between the structural members and comprise the same deformable material as the structural members but of a different thickness than the structural members.

In an embodiment the deformable, implantable port comprises mesh, webbing or a sheet of a deformable material with an orifice therethrough that spans the space defined by the port perimeter member to comprise a port base surface.

In an embodiment the deformable, implantable port comprises an upper surface of the port contour that comprises or is covered by a tissue ingrowth material.

In an embodiment the deformable, implantable port is generally dome-shaped.

In an embodiment the deformable, implantable port is substantially flat.

In an embodiment the deformable, implantable port further comprises a gripping element disposed on the frame structure.

In an embodiment the deformable, implantable subcutaneous medical device has a passageway therethrough for accommodating an elongated transcutaneous component that, in use, extends from outside a patient's body, through a skin opening, into and through the medical device positioned at an implantation site, and then to an internal body location, and the medical device comprises: a device body portion having an original device shape and comprising a deformable material and/or having a deformable structure whereby, at the completion of a period of use in a patient's body, the implanted device body portion can be collapsed, compressed, folded, stretched, elongated and/or twisted into a modified device shape dimensioned and oriented for removal from the implantation site through a skin opening that is substantially smaller than the largest dimension of the original device shape.

In an embodiment the deformable, implantable medical device has a device body portion that comprises a frame or cage-like structure comprising interconnected structural members that define a body portion perimeter, a body portion orifice, and a body portion contour that extends between the body portion perimeter and the body portion orifice.

In an embodiment the deformable, implantable medical device comprises a frame that has an appropriate balance of device body portion rigidity and springiness to gently support and cushion the tissue adjacent the implanted medical device.

In an embodiment the deformable, implantable medical device has a device body portion that can be collapsed, compressed, folded, stretched, elongated and/or twisted into a reduced-size device profile whereby the device can be removed intact from an implantation site through an opening that is about 50% or less than the longest dimension of the original device shape, or that has an area that is about 30% or less than the area of the original device shape, or both.

In an embodiment the deformable, implantable medical device has a device body portion that comprises open spaces between the structural members.

In an embodiment the deformable, implantable medical device comprises spaces between the structural members that define the body portion contour and comprise mesh, webbing or sheets of a deformable material that, because of its composition, its thickness, or both, is more pliable and deformable than the structural members.

In an embodiment the deformable, implantable medical device comprises mesh, webbing or a sheet of a deformable material with an orifice therethrough that spans the space defined by the body portion perimeter member to comprise a body portion base surface.

In an embodiment the deformable, implantable medical device comprises mesh, webbing or sheets that span the spaces between the structural members and comprise a different deformable material than the deformable material of the structural members.

In an embodiment the deformable, implantable medical device comprises an upper surface of the body portion contour that comprises or is covered by a tissue ingrowth material.

In an embodiment the invention comprises a method for removing a deformable subcutaneous port for anchoring a transcutaneous treatment component from a port implantation site comprising the steps of:

(a) removing the treatment component from the port and from a transcutaneous opening adjacent the port wherein the deformable port comprises: a port body portion for receiving the transcutaneous treatment component beneath a point of entry into the physiology of a patient and for routing the transcutaneous treatment component, the port body portion comprising a deformable material and/or having a deformable structure with a port perimeter that defines a normal area port footprint and a port orifice through which the transcutaneous treatment component enters the port body portion; wherein the port body portion has a composition and/or structure that enables the implanted port to be collapsed, compressed, folded, stretched, elongated and/or twisted into a modified port shape having a reduced-size port profile whereby the port can be removed intact or piecemeal from the physiology of the patient through an opening that is substantially smaller than the normal area port footprint;

(b) inserting a retrieval implement through the transcutaneous opening;

(c) grasping the port body portion with the retrieval implement;

(d) applying a port distortion force to the port body portion with the retrieval implement to collapse, compress, fold, stretch, elongate and/or twist the port body portion into a modified port shape having a reduced-size port profile along an axis generally in alignment with the transcutaneous opening; and, (e) withdrawing the port body portion having the modified port shape through the transcutaneous opening.

These and other features and advantages of embodiments of the present invention are described in greater detail below with reference to the following figures.

BRIEF DESCRIPTION OF THE DRAWINGS

FIG. 7C depicts a perspective view of an embodiment of an implantable subcutaneous port of the present invention during a stage of removal.

FIG. 9A depicts a cross-sectioned end view of an embodiment of an implantable subcutaneous port of the present invention.

FIG. 9B depicts an end view of an embodiment of an implantable subcutaneous port of the present invention.

DETAILED DESCRIPTION

Figure 1:
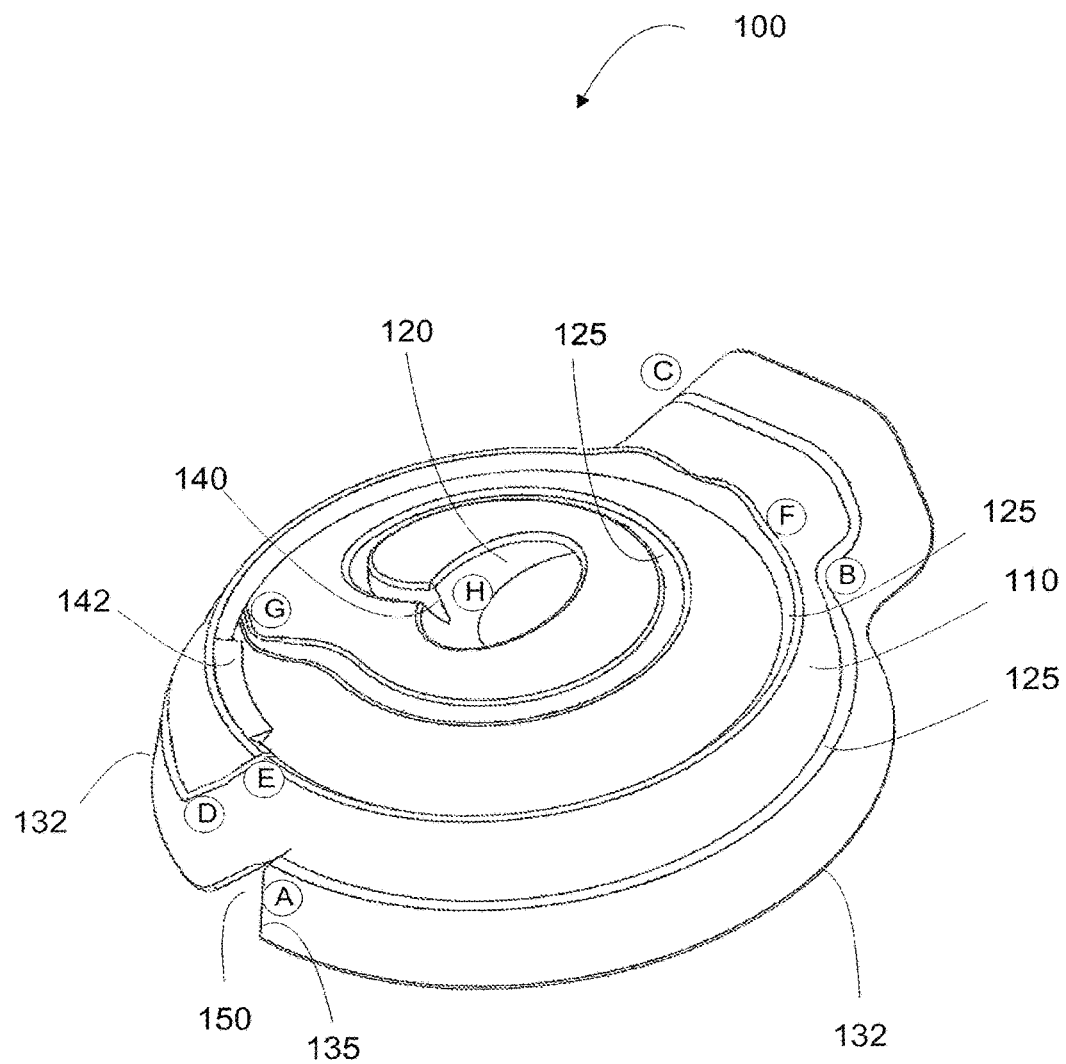
FIG. 1 depicts a perspective view of an embodiment of an implantable subcutaneous port of the present invention.

The present invention generally provides a medical device that is capable of implantation within a patient for long-term treatments. The device of the present invention includes a base, or port, having a port orifice, that functions as a deformable implanted medical port capable of receiving, routing, and anchoring a treatment component, such as for example a catheter shaft, fluid conduit, power cable or fiber optic cable, that extends through the patient's skin, through the port orifice and into the patient's internal physiology. The port is deformable and fabricated from deformable material, as defined herein, for facilitating removal from an implantation site either with or without frangible lines. The port also is shaped to maximize comfort and ease of installation. In some embodiments, the port is relatively flat or dome shaped. In some embodiments, the port has a generally oval-shaped or rounded geometry when viewed from the top. The port further may comprise at least one tissue ingrowth surface that helps further anchor the device and establish a biological seal between living tissue and an implanted port.

As defined and used herein, the term "deformable port" means a medical port that comprises structure and/or composition that provides adequate stability for the port when it is in use, as well as sufficient deformability characteristics to facilitate intact or piecemeal removal after use of the port is completed.

As defined and used herein, the term "deformable port" is meant to include a port fabricated from deformable material that, at the time of removal of the port from an implantation site, has sufficient flexibility, elasticity and/or pliability such that the port can be compressed, folded, stretched, elongated and/or twisted into a modified port shape having a reduced-size profile along an axis so that the port having the modified port shape and the reduced-size port profile can be removed intact through an incision or opening that is substantially smaller than the size of the port in its undistorted form.

The deformable material used for fabricating the deformable port may have the requisite deformability characteristics at the time the port is implanted, or alternatively, it may develop those deformability characteristics in situ, for example by a process of biodegradation or bioabsorption.

As defined and used herein, the term "deformable port" is also meant to include a port fabricated from a deformable material with structural features that enhance stability of the port in use while preserving deformability characteristics of the port. For example, the port body portion may have variable wall thicknesses, for instance thicker wall sections around the perimeter and along structural ribs that define the contour of the port for operational stability, and thinner, more pliable wall sections, or in some embodiments no wall sections at all, inward from the port perimeter spanning the open spaces between the perimeter structural member and the rib elements.

Alternatively, the thinner wall sections of the port body portion may define one or more narrow regions, boundaries or lines within the port body portion which are herein referred to as "frangible lines" or "boundary lines." Such boundary lines define weaker and/or thinner wall areas that are more flexible than other wall sections of the port body portion, which facilitates collapsing, folding and/or twisting the port along those boundary lines. In some embodiments, the port body portion is susceptible to fracturing and tearing along one or more of those frangible or boundary lines to facilitate unraveling and/or piecemeal removal of a port from an implantation site.

As discussed above, the terms "frangible line" or "boundary line" are used interchangeably herein in reference to, and are meant to include, all types of port configurations and constructions in accordance with this invention wherein the sides of the port comprise some thicker, stronger and/or less deformable port regions (herein "first port regions") separated by thinner, weaker and/or more pliable port regions or by completely open regions (herein "second port regions"). A boundary or a boundary line between first port regions having similar deformability characteristics is defined by the second port regions having the different deformability characteristics.

It will be understood that the meanings of the terms "first port regions" and "second port regions" as used above relating to port deformability characteristics are relative and could be reversed without affecting the above definitions of the terms "frangible line," "boundary line" and "boundary." In other words, the "first port regions" could be the more-readily deformable regions relative to the deformability characteristics of the "second port regions," or vice versa.

Figure 2:
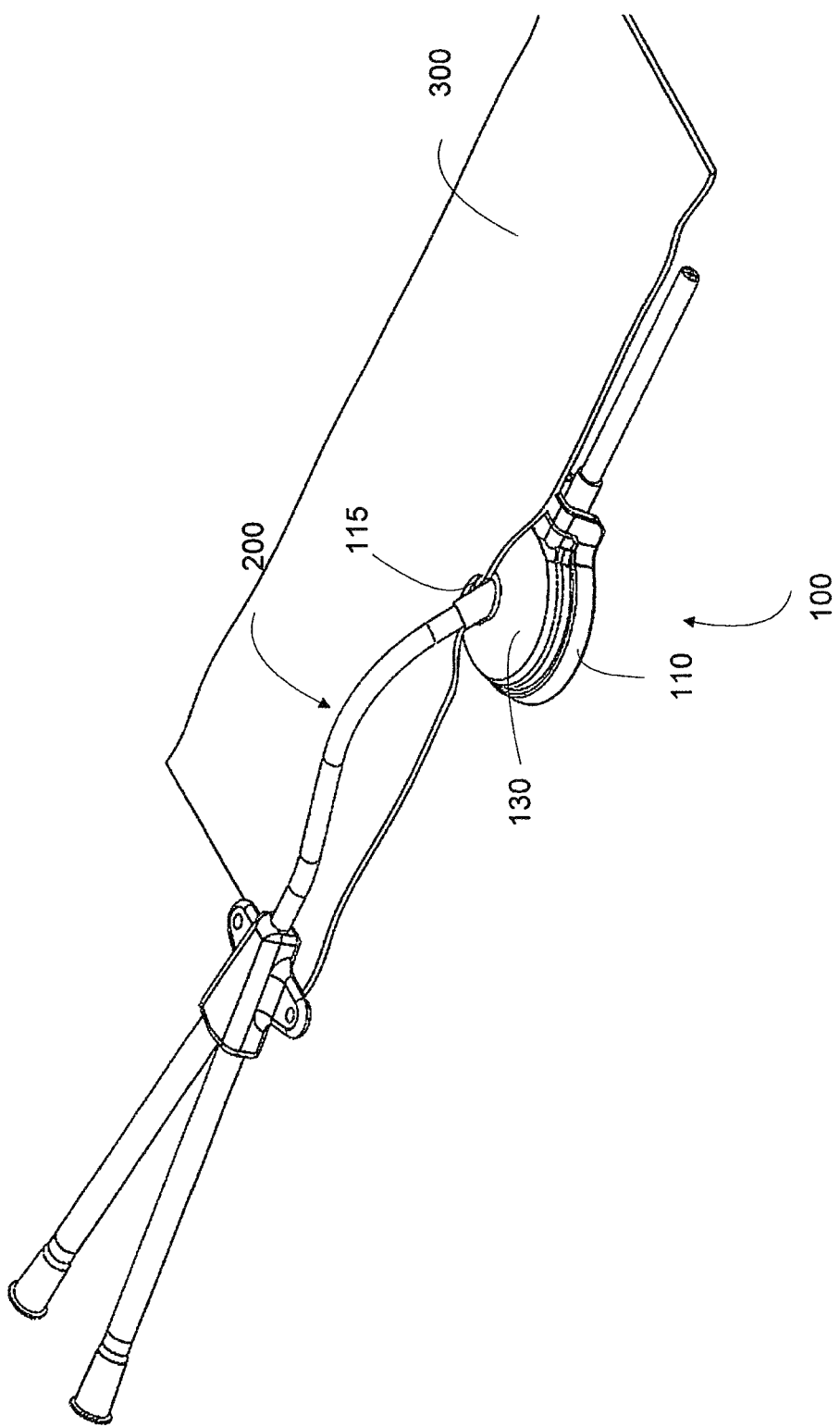
FIG. 2 depicts a perspective view of an embodiment of an implantable subcutaneous port of the present invention in use.
Figure 3:
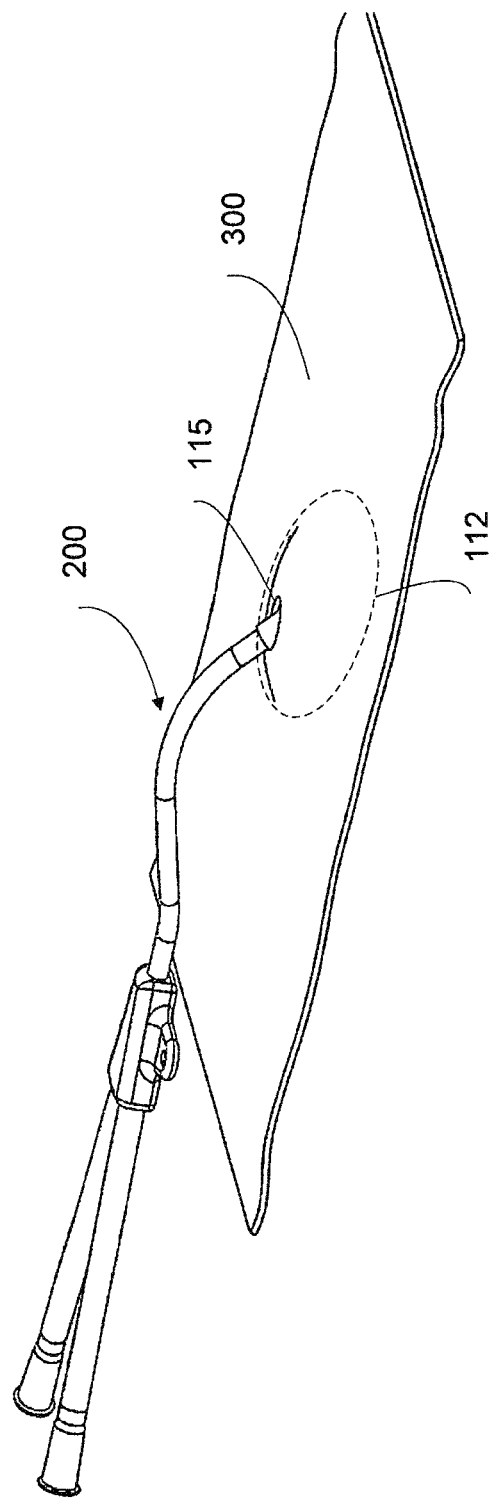
FIG. 3 depicts a perspective view of an embodiment of an implantable subcutaneous port of the present invention in use.

Taking FIGS. 1 through 3 together, an embodiment of the deformable, implantable subcutaneous port 100 of the present invention comprises a port body portion 110 for anchoring a transcutaneous treatment component 200. In all embodiments, the port body portion 110 may be generally dome shaped or flat. The port body portion 110 receives the transcutaneous treatment component 200 beneath the point of entry 115, which may be an incision in a dermal layer 300 of a patient's skin, and routes the transcutaneous treatment component into the physiology of the patient. The port body portion 110 preferably is produced from a deformable polymer material for example, such as but not limited to, polyurethane, silicone, or any soft material having a durometer between 40 on the Shore A scale and 70 on the Shore D scale. In some embodiments, the port body portion 110 has a normal area port footprint 112, and defines an orifice wall 120 through which the treatment component 200 enters the port body portion 110. Like a conduit, the orifice wall defines an orifice through which the transcutaneous component passes. In an embodiment, the orifice wall is generally annular in shape and defines a generally round orifice for accommodating a generally cylindrically shaped transcutaneous treatment component, but other embodiments may comprise an orifice wall defining a rectangle, hexagon, slit or any other geometric configuration suitable for the passage of a particularly shaped treatment component. The embodiment of the deformable, implantable subcutaneous port 100 of FIG. 1 comprises an annular orifice wall 120 deforming a substantially round opening into the port body portion 110. The orifice wall 120 is disposed at the top (skin-facing) side of the port body portion 110 for positioning beneath the opening through the dermal layer 300 that defines the point of entry 115 of the transcutaneous treatment component 200.

Figure 4:
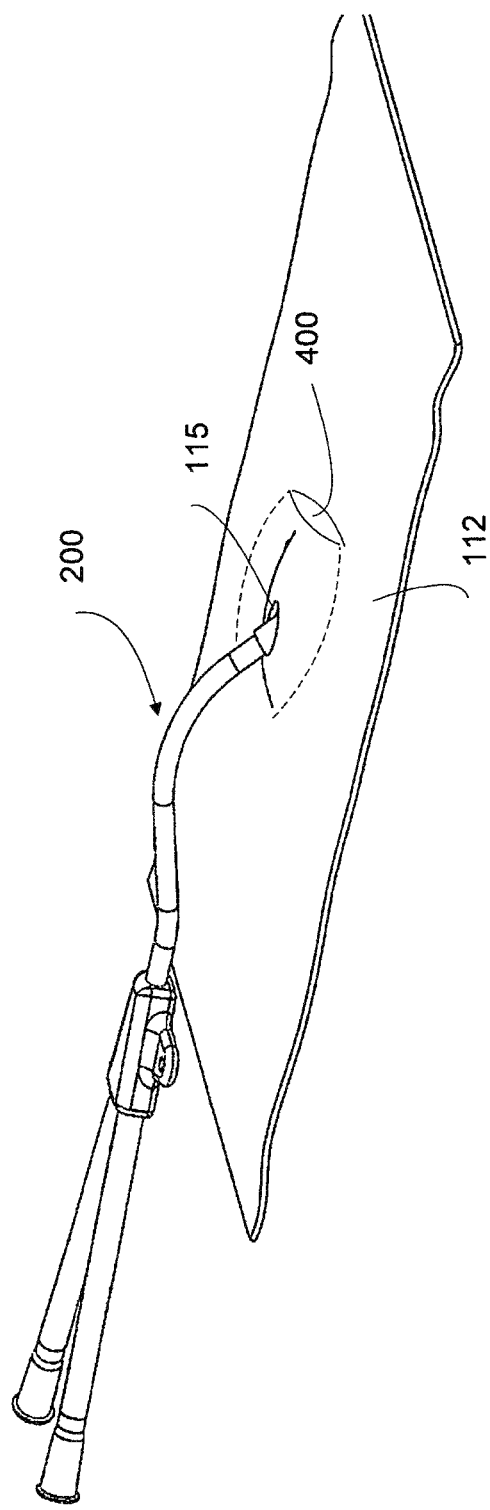
FIG. 4 depicts a perspective view of an embodiment of an implantable subcutaneous port of the present invention in use.
Figure 5A:
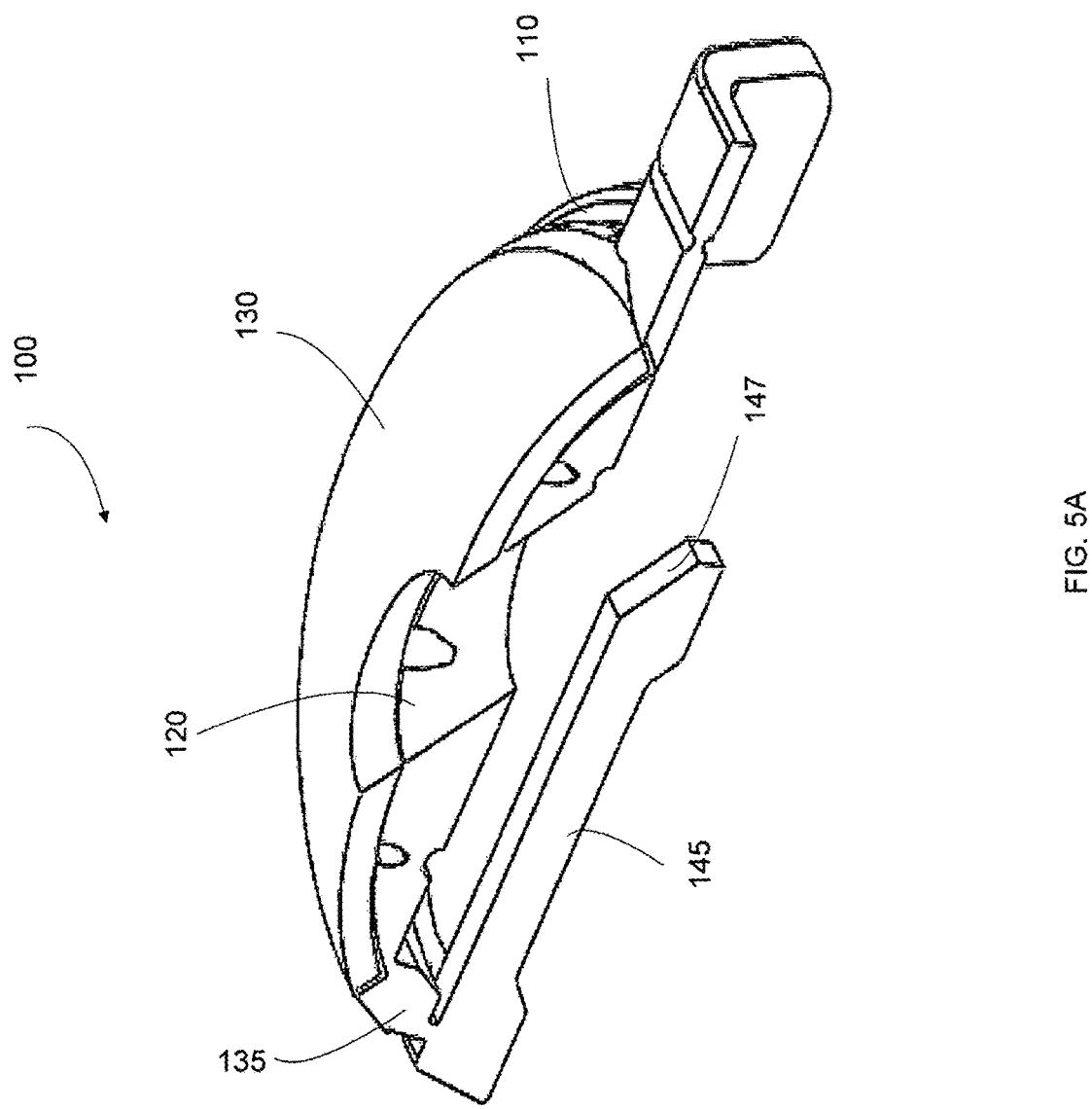
FIG. 5A depicts a perspective cross section of an embodiment of an implantable subcutaneous port of the present invention.
Figure 5B:
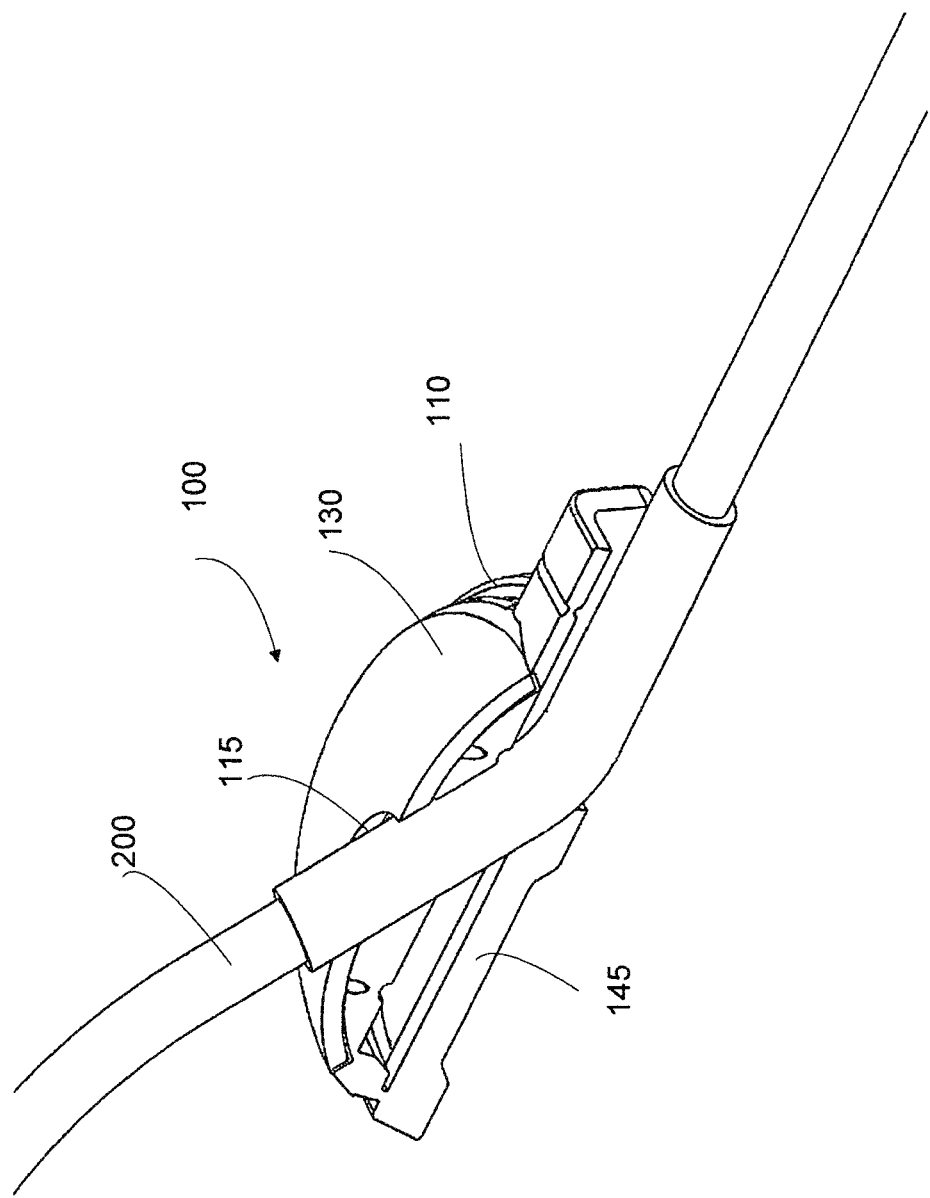
FIG. 5B depicts a perspective cross section of an embodiment of an implantable subcutaneous port of the present invention.

In an aspect, the deformable, implantable subcutaneous port 100 may comprise one or more frangible or boundary lines 125 formed within the port body portion, which enables removal of the port body portion 110 from the inner physiology of a patient through a transcutaneous opening defining an area of less than about thirty percent of the normal area port footprint 112 of the port body portion 110 with or without tearing along those boundary lines. Furthermore, in some embodiments, the longest dimension of the transcutaneous opening is no more than about 50 percent of the longest dimension of the major plane of the port body portion. In an embodiment, the transcutaneous opening is the point of entry 115 of the transcutaneous treatment component 200. In another embodiment, the transcutaneous opening is an incision 400 adjacent the port body portion 110, as indicated in FIG. 4. Preferably though, the length of the incision 400 is no greater than about 50 percent of the longest dimension of the port body portion 110. For example, the embodiment of the port body portion 110 of FIGS. 1A through 4 is generally round and has a longest dimension along its diameter. The length of an incision therefore would preferably not need to be greater than half of the diameter of the port body portion 110. Limiting the size of the incision 400 reduces the amount of trauma inflicted on the patient, thereby reducing the risk of infection.

Figure 8:
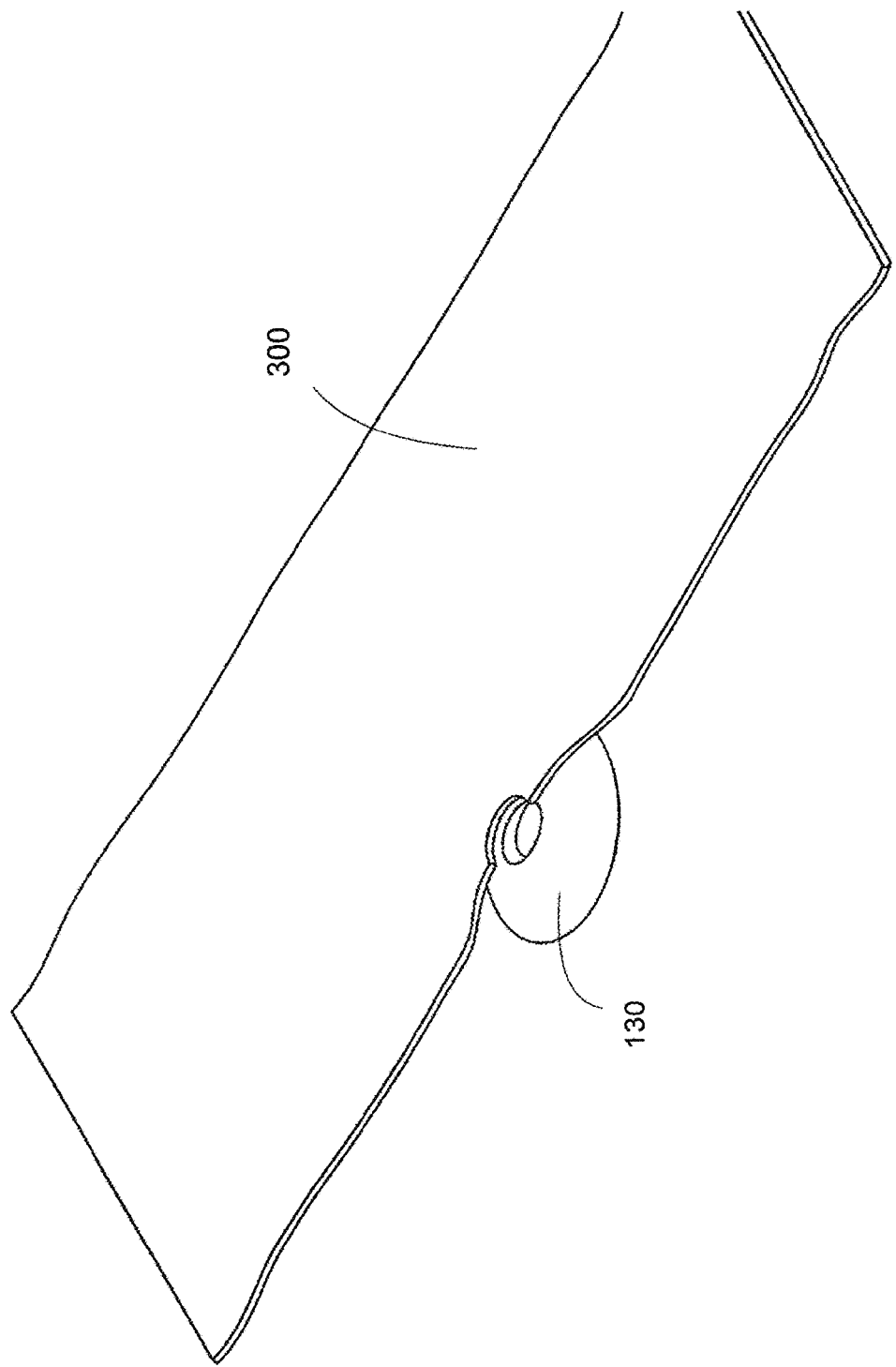
FIG. 8 depicts a top perspective view of a portion of an embodiment of an implantable subcutaneous port of the present invention.

The implantable subcutaneous port 100 may further comprise a tissue ingrowth skirt or scaffold 130 made at least partially from a tissue ingrowth material (e.g., Dacron™) and disposed along a surface of the port body portion or along the contour defined by a port frame structure about the orifice wall 120. This placement promotes tissue ingrowth into the tissue ingrowth skirt 130 around the point of entry 115 of the transcutaneous treatment component 200 so that a biological seal forms that helps protect against infectious pathogens. In an embodiment, the tissue ingrowth skirt 130 may be partially or completely bioabsorbable so that any portion remaining behind after removal of the port will safely degrade. In all embodiments having a tissue ingrowth skirt 130, following a period of tissue ingrowth, the force required to separate the port body portion 110 from the tissue ingrowth skirt 130 is less than the force required to remove the tissue ingrowth skirt 130 from the adjacent dermal layer 300. This enables removal of the port body portion 110 while leaving behind part or all of the tissue ingrowth skirt 130, as indicated in the embodiment depicted in FIG. 8.

Returning now to the configuration of the one or more frangible or boundary lines 125, placement of the one or more frangible or boundary lines 125 along the port body portion 110 enables a clinician in some invention embodiments to fracture and separate the port body portion 110 into one or more lengths or sections for removal through a transcutaneous opening that is relatively smaller than the dermal incision required for placing the entire subcutaneous implantable port 100 at the outset of patient treatment. In certain embodiments, the port body portion 110 is removable through the point of entry 115 of the transcutaneous treatment component 200 following removal of that treatment component. Because of the elimination of any additional incision, such embodiments may prevent a patient from experiencing further trauma, and further reduce risk of infection and other risks associated with surgical procedures.

Figure 7A:
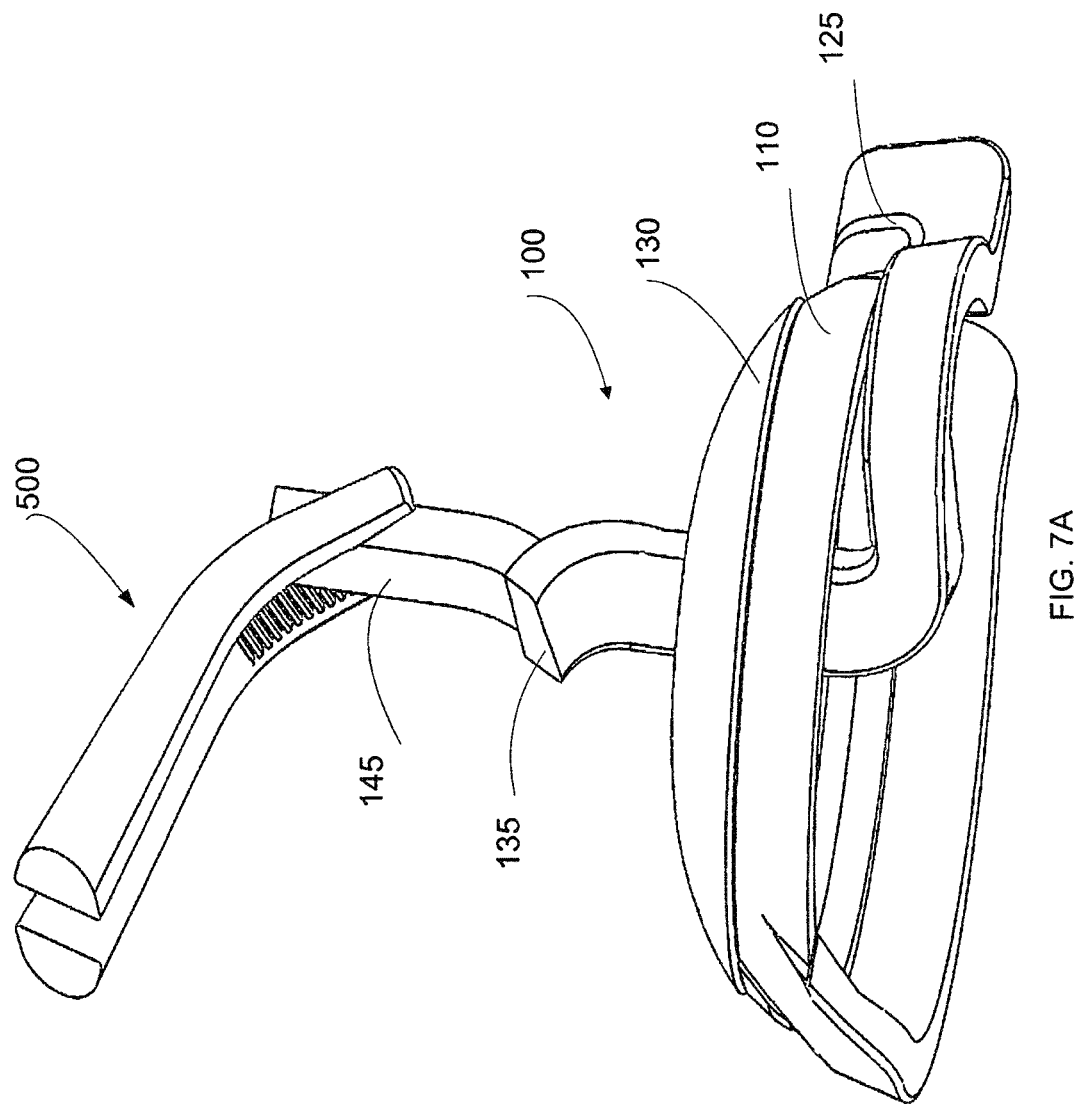
FIG. 7A depicts a perspective bottom view of an embodiment of an implantable subcutaneous port of the present invention during a stage of removal.
Figure 7B:
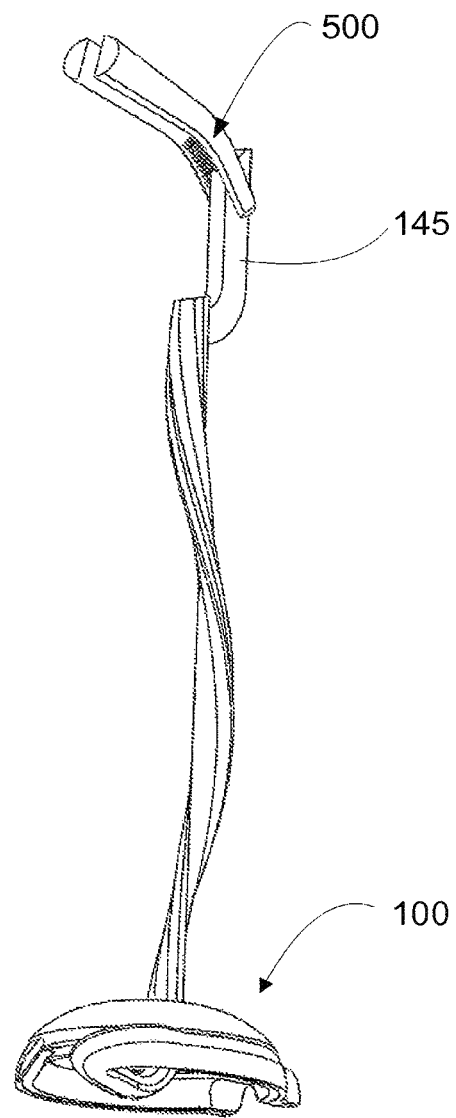
FIG. 7B depicts a perspective top view of an embodiment of an implantable subcutaneous port of the present invention during a stage of removal.

In an embodiment, the one or more frangible or boundary lines 125 may form one or more paths extending between the orifice wall 120 and the outer perimeter 132 of the port body portion 110 so that the port body portion 110 is sectioned by the one or more frangible or boundary lines 125. The one or more paths of the one or more frangible or boundary lines 125 may be intersecting and/or non-intersecting so as to divide the port body portion 110 into sections or pieces sized for removal through a relatively small transcutaneous opening. In an embodiment, the one or more frangible or boundary lines form a continuous path extending between the orifice wall 120 and an outer perimeter 132 of the port body portion 110. For example, in an embodiment shown in FIG. 1, the frangible or boundary lines 125 may form one or more spirals wound around the orifice defined by the orifice wall 120 and spanning between the orifice wall 120 and the outer perimeter 132. This embodiment enables a clinician to collapse, fold or in some embodiments to fracture and separate the port body portion 110 along the frangible or boundary lines 125 and, in some embodiments, to uncoil the port body portion 110 for removal in one or more long, thin strips, as depicted for example in FIGS. 7A through 7C. In yet another embodiment (not shown), the one or more frangible or boundary lines 125 form one or more paths across the major plane of the port body portion 110, extending between two points on the outer perimeter and thereby sectioning the port body portion 110 into two or more adjacent wall sections.

In another embodiment (not shown), the port body portion 110 is dome shaped and the one or more frangible or boundary lines 125 form one or more closed circuitous paths in the major plane of the port body portion 110, thereby sectioning the port body portion 110 into two or more stacked sections. In a similar embodiment (not shown) the port body portion 110 is substantially flat and the one or more frangible or boundary lines 125 form one or more closed circuitous paths in the major plane of the port body portion 110, thereby sectioning the port body portion 110 into two or more nested sections. Because the port body portion 110 is made from a deformable material, the two or more stacked or nested sections are at least partially collapsible for facilitating removal intact through a transcutaneous opening having an area no larger than about 30 percent of the normal area port footprint 112. In embodiments where the port body portion 110 is removed through the point of entry 115 of the transcutaneous treatment component 200, the area of that transcutaneous opening may be as little as 10 to 15 percent of the normal area port footprint 112 of the port body portion 110.

As indicated in FIG. 1, in certain embodiments, the one or more frangible or boundary lines 125 each have a pulling end 135 and a terminal end 140. The pulling end 135 enables a clinician to initiate a fold and/or tear along the one or more frangible or boundary lines 125 at a particular graspable point on the port body portion 110. The embodiment of FIG. 1 also comprises a stiffener 142 disposed on the port body portion 110 between the pulling end 135 and the terminal end 140. The stiffener 142 may be a localized thickening of the port body portion 110 or an appended element disposed on and integrated with the port body portion 110 for assisting with directing tear propagation along the one or more frangible or boundary lines 125. In effect, the stiffener 142 prevents shearing or tearing along an area of the port body portion 110 located between two relatively closely-spaced portions of the frangible or boundary lines 125. For example, in the embodiment of FIG. 1, tearing begins at the pulling end 135 along the frangible or boundary lines 125 in the direction of location A. The tear propagates to location B and location C, wraps around the port body portion 110 and turns a sharp corner between D and E. At point E, the tear could propagate in either of two directions if not for the presence of the stiffener 142. The stiffener 142 prevents tearing in an undesired direction and forces propagation of the tear in the direction of points F, G and eventually H, located at the terminal end 140. In the embodiment of FIG. 1, the stiffener 142 therefore assists with fully unraveling the port body portion 110 for easy removal in one long, narrow strip.

In some embodiments, the deformable, implantable subcutaneous port 100 further comprises a gripping element 145 disposed on port body portion 110 adjacent the pulling end 135, as depicted in FIGS. 5A through 7C. In the embodiment of FIGS. 5A through 7C, the gripping element 145 extends within the normal area port footprint 112 of the port body portion 110, starting at an outer perimeter 132 of the port body portion and extending up to an inserted transcutaneous treatment component 200. In the embodiment of FIGS. 5A through 7C, the gripping element 145 extends from the outer perimeter 132 of the port body portion 110, but, alternatively, the gripping element 145 may extend from any point on the port body portion 110. For example, the gripping element 145 may be disposed on the port body portion 110 at a point located directly beneath the orifice wall 120 for increased accessibility as compared to the embodiment where the gripping element 145 is located closer to the outer perimeter 132 and therefore deeper within the physiology of the patient. In another embodiment, the gripping element may extend beyond the normal area port footprint 112 of the port body portion 110.

In some embodiments, the gripping element 145 may terminate in a contoured end 147 for accommodating the contours of the adjacent transcutaneous treatment component 200 and/or for assisting with directing the treatment component into the physiology of a patient. In the embodiment of FIGS. 5A through 7C, the gripping element 145 terminates at a contoured end 147 reachable through the orifice defined by the orifice wall 120. As FIG. 5B clearly depicts, the contoured end 147 directs an inserted treatment component through the port body portion 110 at a desired angle. Following removal of the treatment component, a clinician may insert a retrieval implement 500, such as forceps or tweezers, through the orifice defined by orifice wall 120 for grasping the gripping element 145 and pulling that gripping element 145 up through the orifice and out of the patient with the port body portion 110 in tow. Gripping the gripping element 145 from a point external to the physiology of a patient and applying a port distortion force to the port body portion 110 results in collapsing, compressing, folding, stretching, elongating and/or twisting the port into a modified port shape, or in some embodiments fracturing and tearing the one or more frangible or boundary lines 125 and unraveling the port body portion 110 along those lines 125. Applying a slight torque or twisting motion during the application of the port distortion force may assist in stretching, twisting and/or fracturing along the lines 125. In some embodiments, a notch 150 disposed near the pulling end 135 and adjacent the intersection of the pulling end 135 and the gripping element 145 may assist with the initial propagation of a tear along the frangible line 125. FIGS. 9A and 9B depict such an embodiment.

Alternatively, in certain embodiments (not shown), the port body portion 110 may comprise one or more puncture points, or relatively thin wall sections, that enable a clinician to puncture the port body portion 110 with an implement at a point near the lines 125. The clinician then may grasp the wall of the port body portion 110 with the retrieval implement 500, and pull on the port body portion 110 to initiate a tear along the lines 125. This puncture technique may be particularly useful in embodiments such as those described above having lines 125 forming closed circuitous paths in the port body potion 110 and thereby separating the port body portion 110 into two or more stacked sections. Those embodiments, however, may benefit from the inclusion of one or more gripping elements 145 as described above. In all embodiments, the gripping element 145 may be disposed on the port body portion 110 so that tears propagate along the lines 125 in more than one direction, starting from the point of intersection of the gripping element 145 (or puncture point) and the lines 125. Additionally, some embodiments of the port body portion 110 may further comprise radiopaque or ultrasonically detectable markers disposed at various points along the port body portion 110 to enable a clinician to determine whether or not the entire port body portion 110 has been successfully removed.

As described above, the port body portion 110 is made of a deformable material having a durometer that enables collapsing, compressing, folding, stretching, elongating and/or twisting the port into a modified port shape having a reduced-size port profile, or in some embodiments fracturing and separating the port body portion along the lines 125 under an application of port distortion force and that enables a sufficient amount of deformation of the port for removal of the port body portion 110 intact or in one or more sections delineated by the lines 125. Spacing between the lines 125 is adjustable in accordance with material selection and, in particular, material elasticity. A proper combination of material selection and spacing between the lines 125 prevents shearing or yielding of the unraveling section of the port body portion 110 under an application of port distortion force as required for removal through a relatively small transcutaneous opening, such as the point of entry 115 of the transcutaneous treatment component into the physiology of a patient.

One skilled in the art could form the one or more boundary or frangible lines 125 as defined above within the port body portion 110 using numerous manufacturing techniques. For example, the port body portion 110 may be injection molded with the one or more boundary/frangible lines 125 cast therein, or the one or more boundary/frangible lines 125 may be etched into the formed port body portion 110. In some embodiments, the boundary/frangible lines 125 oppose one another and are formed on both the top wall surface and the underside wall surface of the port body portion 110, such that a reduction in port wall thickness along this boundary occurs from both sides of the port. This type of manufacture is indicated, for example, in the cross section view of the embodiment of the deformable, implantable subcutaneous port 100 depicted in FIG. 9A.

In addition to applying injection molding and etching techniques as described above, selective weakening of boundary wall regions of the port body portion 110 along the boundary/frangible lines 125 also could be accomplished by other fabrication processes including, but not limited to, serial perforation, chemical etching, mechanical skiving, mechanical scoring, or other such methods as are known to those skilled in the art. The boundary/frangible lines 125 could also be formed using a localized heat treatment that changes the crystalline structure of the deformable port material along the boundaries, thereby reducing the port distortion forces required to collapse, compress, fold, stretch, elongate, twist and/or fracture and separate the port body portion 110 at those specific locations.

One skilled in the art also could apply heat treatments to reflow the material of the port body portion 110 to form a berm on either side of the boundary lines 125, thereby creating a larger gradient between the port distortion force required to distort the port body portion 110 generally and the force required to distort the port body portion 110 along the boundaries 125. In another embodiment, one skilled in the art could injection mold such a berm into the port body portion 110 along at least select sections of the boundaries 125, thereby providing further directional control over port distortion. In some embodiments, localized thickening of the port body portion 110 on either side, both sides, or alternating sides of the boundaries 125 provides further control over port distortion along those boundaries. In yet another embodiment, the port body portion 110 comprises materials that are highly degradable and/or bioabsorbable at least in localized areas or along particular boundaries. In this embodiment, the port body portion 110 has a substantially uniform wall thickness during initial placement within the physiology of a patient, but, over time, the degradable or absorbable material weakens the port body portion 110 in localized areas, thereby creating the boundaries.

Figure 10:
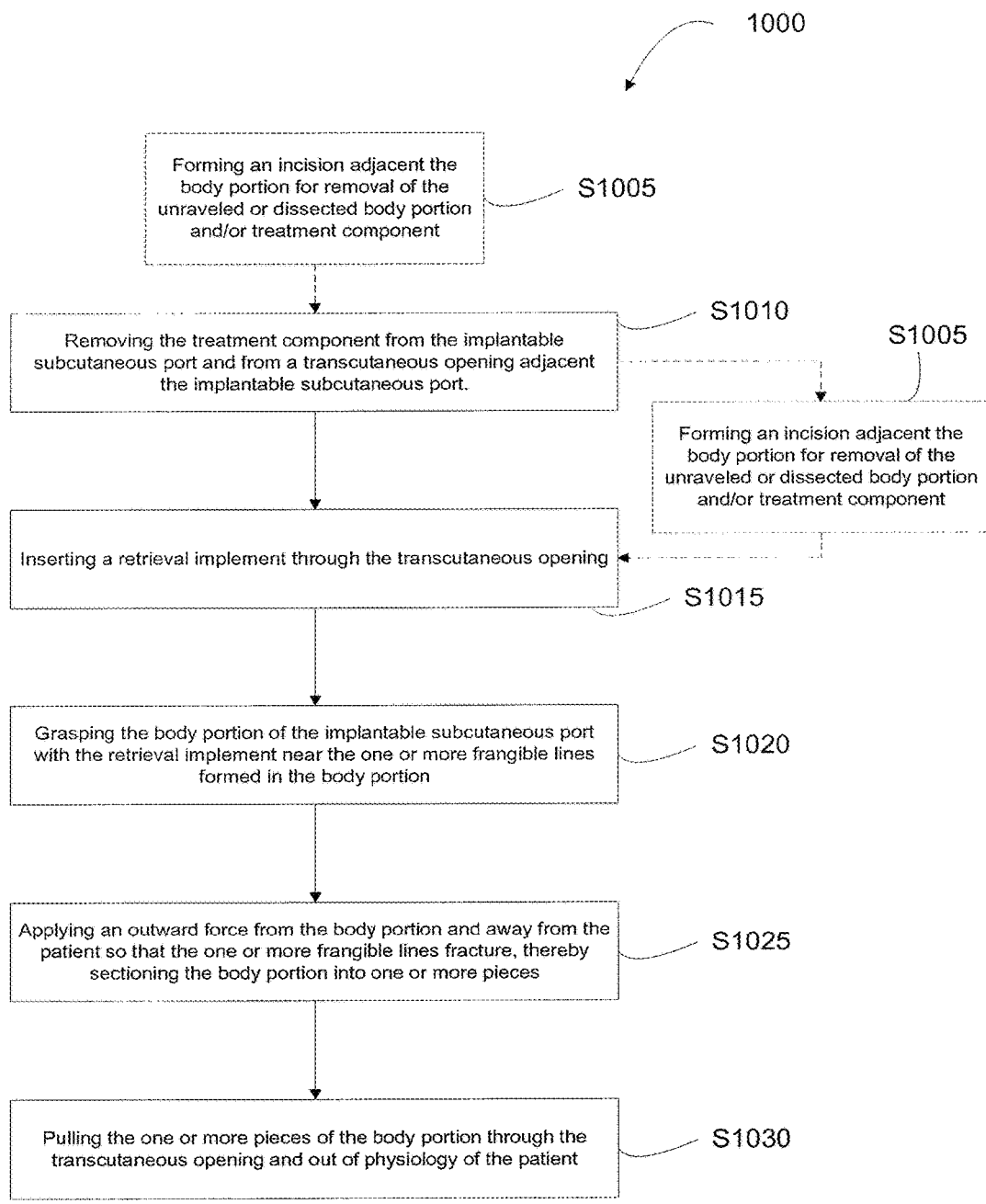
FIG. 10 depicts a schematic of an embodiment of a method of removing an implanted subcutaneous port.

Turning now to FIG. 10, the present invention also comprises a method 1000 of removing a deformable, implantable subcutaneous port 100 for anchoring a transcutaneous treatment component 200. In a first step S1010, the method 1000 of removing the port comprises removing the treatment component 200 from the deformable, implantable subcutaneous port 100 and from a transcutaneous opening adjacent the port. The implantable subcutaneous port 100 comprises a port body portion 110 for receiving the transcutaneous treatment component 200 beneath the point of entry 115 into the physiology of a patient. The port body portion 110 is formed from a deformable material and has a normal area port footprint 112 defined by the outer perimeter 132 of the deformable, implantable subcutaneous port 100. The port body portion 110 comprises an orifice wall 120 defining an orifice through which the transcutaneous treatment component 200 enters into the port body portion 110, which further routes the treatment component 200 into the physiology of the patient. In some embodiments, the deformable, implantable subcutaneous port 100 may comprise boundaries 125 formed within the port body portion 110, such that application of port distortion forces along or proximate to those boundaries distorts the shape of the port and enables the removal of the port body portion 110 from the physiology of a patient through a relatively small transcutaneous opening, such as the point of entry 115 of the transcutaneous treatment component 200. A clinician may alternatively remove the port body portion 110 through an alternate transcutaneous opening, such as a relatively small incision 400 in the dermal layer 300 adjacent the port body portion 110. In any embodiment, the transcutaneous opening typically spans an area of less than about thirty percent of the normal area port footprint 112 of the port body portion 110.

Figure 6:
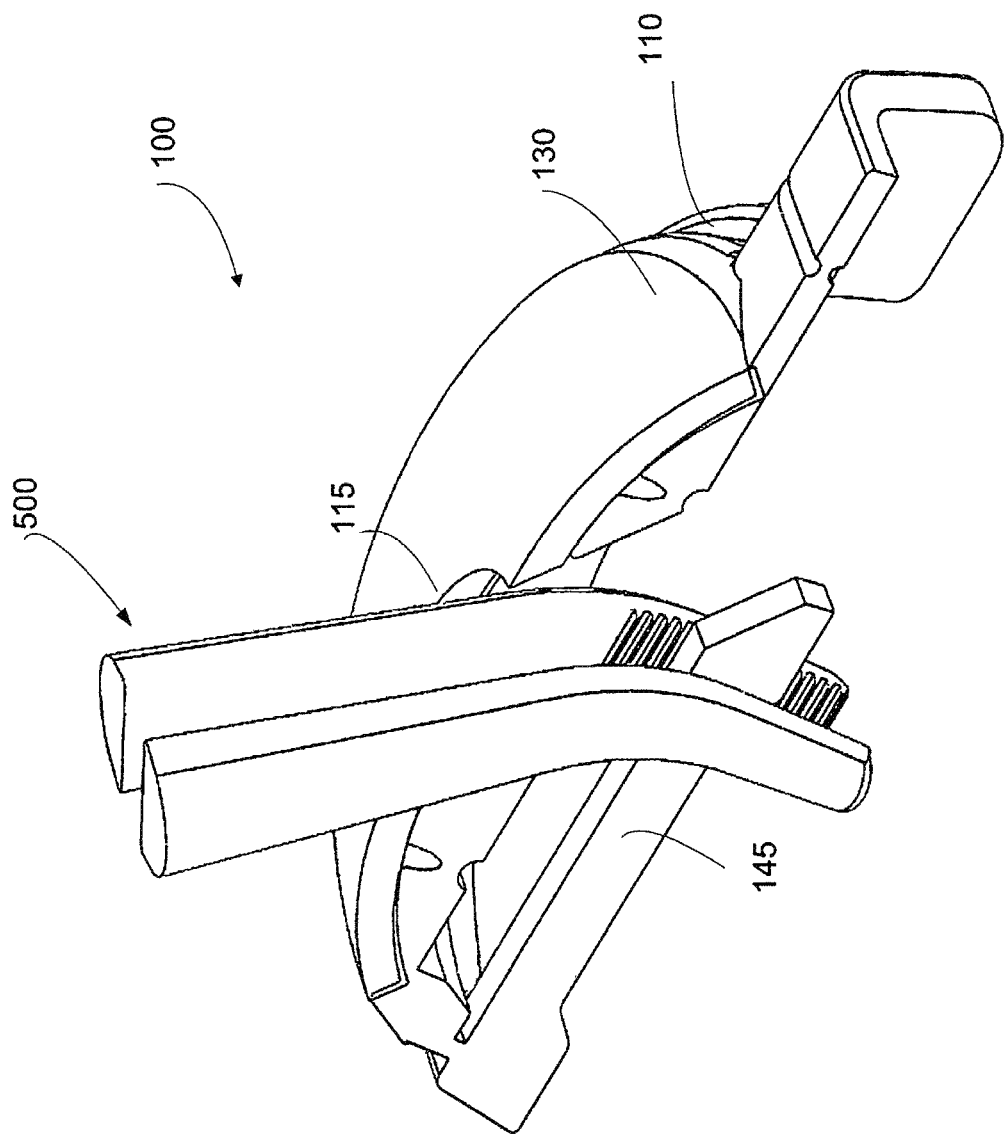
FIG. 6 depicts a perspective cross section of an embodiment of an implantable subcutaneous port of the present invention

A second step S1015 in the removal method comprises inserting a retrieval implement 500 through the transcutaneous opening, and a third step S1020 comprises grasping the port body portion 110 with the retrieval implement 500, for example near the boundary lines 125. As depicted in FIG. 6, the port body portion 110 may further comprise a gripping element 145 disposed adjacent to the one or more boundary lines, wherein gripping the gripping element 145 from a point external to the physiology of a patient and applying port distortion force to the port body portion 110 results in collapsing, compressing, folding, stretching, elongating, twisting or, in some embodiments, fracturing and separating the port body portion along the boundary lines 125. The method 1000 of removing the port may further comprise an incising step S1005 prior to and/or following the first step S1010 of removing the treatment component. The optional incising step S1005 comprises a clinician forming an incision adjacent the port body portion 110 for removal of the port body portion 110 and/or the treatment component 200.

In some embodiments, fracturing of the port along the boundary lines 125 resizes the port body portion into one or more sections sized for removal through the relatively small transcutaneous opening, which preferably has a longest dimension no greater than fifty percent of the longest dimension of the normal area port footprint 112. The boundary lines 125 may be configured in any number of patterns as described above with regard to embodiments of the deformable, implantable subcutaneous port 100. In an alternate embodiment, also described above, the port body portion 110 comprises no gripping element 145, but instead comprises one or more areas of weakness and/or enhanced deformability defined by thinned port wall sections or, in the port frame structure embodiment, no wall sections at all.

A fourth step S1025 in the method comprises applying a port distortion force to the port body portion 110 so that the port body portion 110 is transformed into a modified port shape having a reduced-size port profile to facilitate removal from the implantation site. As further indicated in the embodiment of FIGS. 7A through 7C, pulling the gripping element 145 further away from the port body portion 110 further distorts and helps to remove the portion of the port body portion 110 attached to the gripping element 145. The method comprises a final step S1030 of pulling the one or more pieces of the port body portion having the modified port shape(s) through the transcutaneous opening, here the point of entry 115, and out of the physiology of the patient. In some embodiments, the method further comprises the step of separating the port body portion 110 from all or part of a tissue ingrowth skirt 130 disposed thereon for promoting tissue ingrowth around the point of entry 115 of the transcutaneous treatment component 200. For example, in the embodiment depicted in FIGS. 7A through 8, the port body portion 110 unravels, leaving behind the entire tissue ingrowth skirt 130 under the dermal layer 300. In some embodiments, this tissue ingrowth skirt 130 is also biodegradable and/or bioabsorbable, along with at least some portions of the port, so that the physiology of the patient dissolves and clears the tissue ingrowth skirt 130 over time. In alternate embodiments the tissue ingrowth skirt 130 can be made of a material that is suitable for use as a permanent implant, such a polyester velour fabric, which is used on a wide range of permanently implanted medical devices.

Figure 11A:
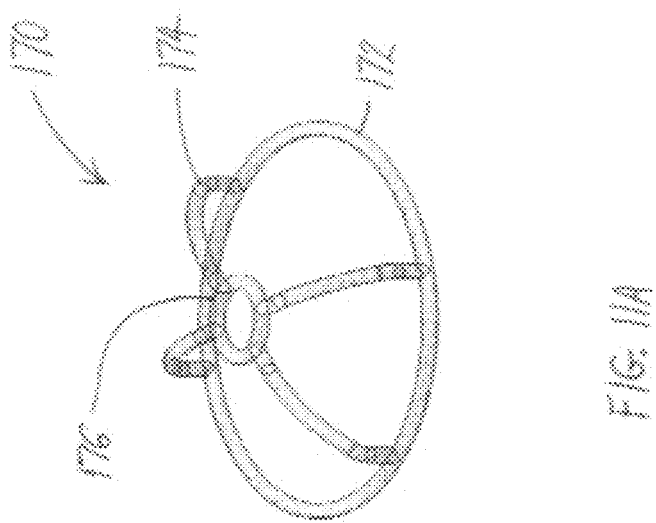
FIGS. 11A, 11B and 11C are alternative views of a deformable, implantable subcutaneous port according to another invention embodiment wherein a port frame or cage-like structure of a deformable material defines the perimeter (or base) and the general contour of the port, and where the open spaces between the structural members of the frame are either left open or, in some embodiments, may be covered by or may comprise webbing, mesh or sheets comprising a deformable material.
Figure 11B:
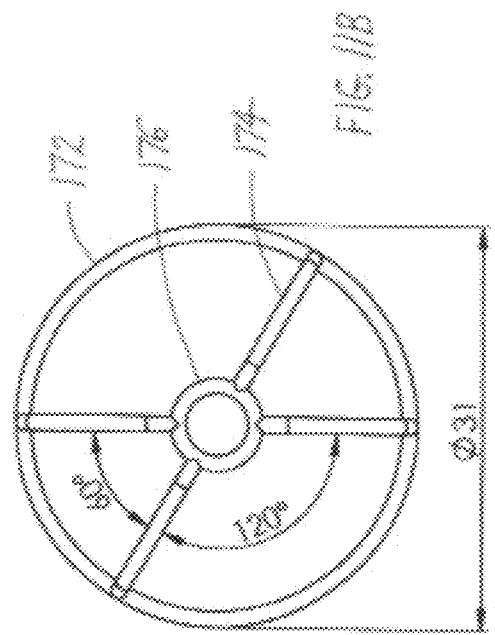
Figure 11C:
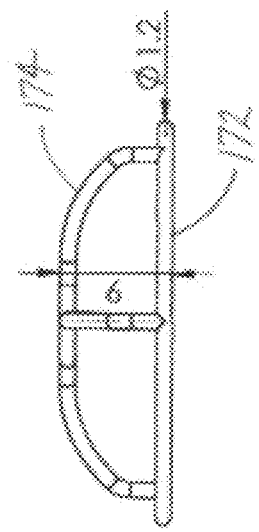

FIGS. 11A, 11B and 11C illustrate another aspect of this invention. FIG. 11A is a schematic perspective view of a deformable port 170 according to this invention and defined by a port frame or cage-like structure. The port frame structure includes a perimeter frame element 172 that defines the base or outer footprint of the port, a ring element 176 that defines the port orifice, and four side or rib elements 174, each of which connects between the perimeter frame 172 and the orifice ring 176. Together, the rib elements 174 define the contour of the upper surface of the port 170.

Although FIGS. 11A to 11C show a particularly configured frame structure with four rib elements 174, it will be understood that frame structures with more than four rib elements or with fewer than four rib elements may be appropriate for a particular port design and application. All of these frame or cage-like structures with any number of structural members and including alternative frame structure configurations are intended to be included within the scope of this invention embodiment.

FIG. 11B is a plan top view of the port 170 of FIG. 11A, and FIG. 11C is a plan side view of the port 170 of FIG. 11A. The port frame elements 172, 174 and 176 comprise a first deformable material, such as a rubber, polymer or other plastic material, that has some structural stability or rigidity in a thickness sufficient to stabilize the outer dimensions of the port when the port is in use. As previously discussed, the port frame structure of FIGS. 11A to 11C preferably has an appropriate balance between rigidity and springiness characteristics such that the structural members apply only gentle and forgiving contact to adjacent tissue while maintaining the dimensional integrity of the port while in use.

In some embodiments of this aspect of the invention, the four-sided open spaces defined by the perimeter frame element 172, the orifice ring 176 and the rib elements 174 are left open, or they are covered only with a layer of tissue ingrowth material. In other embodiments, the frame structure shown in FIGS. 11A to 11C may be covered with, or the open spaces may comprise, thin webbing, mesh or sheets of a second deformable material. Because the frame provides support for the port structure, the webbing or mesh that spans the open spaces of the port frame structure can be very thin, pliable and readily-deformable under port distortion forces. In some embodiments, the frame structure material and the material used to cover or span the open spaces between frame elements may comprise the same deformable material, but the frame elements have sufficient thickness to provide the required port dimensional stability.

While in use, the port 170 provides adequate stability to serve its purpose of receiving, securing in place, and routing a transcutaneous treatment component. When the time comes to remove the port, however, port 170 has sufficient deformability characteristics such that it can be gripped with a suitable instrument, collapsed, and folded, stretched, elongated and/or twisted into a modified port shape having a reduced-size port profile for intact removal of the port through a relatively small opening or incision.

Similar to the invention embodiment described above in connection with FIGS. 5A to 7C, the port 170 of FIGS. 11A to 11C may further comprise a gripping element (comparable to gripping element 145 as seen in FIGS. 5A to 7C) disposed on port 170 to facilitate gripping and distorting the port to a modified port shape in preparation for removing the port from the implantation site. The same description as above relating to the size, shape, positioning and use of gripping element 145 in FIGS. 5A to 7C similarly applies to the frame structure embodiment of FIGS. 11A to 11C.

It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A deformable, implantable subcutaneous port for anchoring a transcutaneous treatment component comprising: a port body portion for receiving the transcutaneous treatment component beneath a point of entry into the physiology of a patient and for routing the transcutaneous treatment component, the port body portion comprising a deformable material and/or having a deformable structure with a port perimeter that defines a normal area port footprint and also with a port orifice through which the transcutaneous treatment component enters the port body portion; wherein the port body portion has a composition and/or structure that enables an implanted port to be collapsed, compressed, folded, stretched, elongated and/or twisted into a modified port shape having a reduced-size port profile whereby the port can be removed intact or piecemeal from the physiology of the patient through an opening that is substantially smaller than the normal area port footprint;

and further wherein the port comprises a frame or cage-like structure comprising interconnected structural members that define the port perimeter, the port orifice, and a port contour that extends between the port perimeter and the port orifice.

2. The deformable, implantable port according to claim 1 wherein the port body portion can be collapsed, compressed, folded, stretched, elongated and/or twisted into a reduced-size port profile whereby the port can be removed intact from an implantation site through a skin opening that is no larger than the size of an opening needed to accommodate the transcutaneous treatment component.

3. The deformable, implantable port according to claim 1 wherein the frame has an appropriate balance of port rigidity and springiness to gently support and cushion the tissue adjacent the implanted port.

4. The deformable, implantable port according to claim 1 wherein the port can be collapsed, compressed, folded, stretched, elongated and/or twisted into a reduced-size port profile whereby the port can be removed intact from an implantation site through an opening that is about 50% or less than the longest dimension of the port in use, or that has an area that is about 30% or less than the normal area port footprint, or both.

5. The deformable, implantable port according to claim 1 wherein the port comprises open spaces between the structural members.

6. The deformable, implantable port according to claim 1 wherein the spaces between the structural members that define the port contour comprise mesh, webbing or sheets of a deformable material that, because of its composition, its thickness, or both, is more pliable and deformable than the structural members.

7. The deformable, implantable port according to claim 6 wherein the mesh, webbing or sheets that span the spaces between the structural members comprise a different deformable material than the deformable material of the structural members.

8. The deformable, implantable port according to claim 6 wherein the mesh, webbing or sheets that span the spaces between the structural members comprise the same deformable material as the structural members but of a different thickness than the structural members.

9. The deformable, implantable port according to claim 6 further wherein mesh, webbing or a sheet of a deformable material with an orifice therethrough spans the space defined by the port perimeter member to comprise a port base surface.

10. The deformable, implantable port according to claim 1 wherein an upper surface of the port contour comprises or is covered by a tissue ingrowth material.

11. The deformable, implantable port according to claim 1 wherein the port is generally dome-shaped.

12. The deformable, implantable port according to claim 1 wherein the port is substantially flat.

13. The deformable, implantable port according to claim 1 wherein the port further comprises a gripping element disposed on the frame structure.

* * * * *